(12) United States Patent
de Josselin de Jong (10) Patent No.: US 9,918,641 B2
(45) Date of Patent: Mar. 20, 2018

(54) FLUORESCENCE FILTER SPECTRUM COMPENSATION

(71) Applicant: Inspektor Research Systems B.V., Amsterdam (NL)

(72) Inventor: Elbert de Josselin de Jong, Bussum (NL)

(73) Assignee: Inspektor Research Systems B.V. (NL)

( * ) Notice: Subject to any disclaimer, the term of this patent is extended or adjusted under 35 U.S.C. 154(b) by 0 days.

(21) Appl. No.: 14/650,299

(22) PCT Filed: Sep. 30, 2013

(86) PCT No.: PCT/IB2013/002791
§ 371 (c)(1),
(2) Date: Jun. 6, 2015

(87) PCT Pub. No.: WO2014/053916
PCT Pub. Date: Apr. 10, 2014

(65) Prior Publication Data
US 2015/0305624 A1    Oct. 29, 2015

Related U.S. Application Data

(60) Provisional application No. 61/708,309, filed on Oct. 1, 2012.

(51) Int. Cl.
*A61C 1/00* (2006.01)
*A61C 3/00* (2006.01)
(Continued)

(52) U.S. Cl.
CPC .......... *A61B 5/0071* (2013.01); *A61B 1/0646* (2013.01); *A61B 1/247* (2013.01);
(Continued)

(58) Field of Classification Search
USPC ...................................................... 433/27, 29
See application file for complete search history.

(56) References Cited

U.S. PATENT DOCUMENTS

| 7,813,787 B2 | 10/2010 | De Josselin De Jong |
| 2004/0023184 A1 | 2/2004 | de Josselin de Jong et al. |

(Continued)

FOREIGN PATENT DOCUMENTS

| CN | 1530073 A | 9/2004 |
| CN | 1671320 A | 9/2005 |

(Continued)

OTHER PUBLICATIONS

Australian Office Action, Examination Report No. 1 for standard patent application, dated Jun. 8, 2017, for application No. AU 2013326222, 5 pgs.

(Continued)

*Primary Examiner* — Nicole F Johnson
(74) *Attorney, Agent, or Firm* — Frost Brown Todd LLC (57) ABSTRACT

A device provides incident light on oral structures, switchably between two states. In the first state, incident light causes autofluorescence of byproducts of decay, and an optical filter between the oral structures and either the user's eyes or a visualizing apparatus yields visually distinguishable appearances for that autofluorescence depending on whether the tissue is healthy or unhealthy. In the second state, the incident light is of a color composition that yields a substantially "white" spectrum after passing through the filter.

15 Claims, 6 Drawing Sheets

(51) Int. Cl.
*A61B 5/00* (2006.01)
*A61B 1/06* (2006.01)
*A61B 1/247* (2006.01)
*F21V 9/08* (2018.01)
*F21V 33/00* (2006.01)
*F21W 131/202* (2006.01)

(52) U.S. Cl.
CPC ............ *A61B 5/0088* (2013.01); *F21V 9/08* (2013.01); *F21V 33/0068* (2013.01); *F21W 2131/202* (2013.01)

(56) References Cited

U.S. PATENT DOCUMENTS

| 2005/0003323 | A1* | 1/2005 | Katsuda | A61B 1/00089 |
| | | | | 433/29 |
| 2008/0062429 | A1* | 3/2008 | Liang | A61B 1/00039 |
| | | | | 356/497 |
| 2008/0063998 | A1* | 3/2008 | Liang | A61B 1/0638 |
| | | | | 433/29 |

FOREIGN PATENT DOCUMENTS

| CN | 101528116 A | 9/2009 |
| EP | 2078493 A2 | 7/2009 |
| JP | 2004-089236 A | 3/2004 |
| JP | 2004-237081 A | 8/2004 |
| JP | 2007-151782 A | 6/2007 |
| WO | 2008033218 | 3/2008 |

OTHER PUBLICATIONS

Chinese Office Action, Notification of Second Office Action, dated May 15, 2017 for Application No. CN 201380051343.4, 7 pgs.
International Search Report and Written Opinion dated Apr. 23, 2014 for Application No. PCT/IB2013/002791, 11 pgs.
Japanese Office Action, Notice of Reasons for Rejection, dated Jul. 19, 2017 for Application No. JP 2015-533715, 23 pgs.
European Patent Office Communication for Application No. EP 13830087.6, dated Sep. 13, 2017.
Mexican Office Action for Application No. MX/a/2015/004158, dated Jun. 22, 2016.

* cited by examiner

FLUORESCENCE FILTER SPECTRUM COMPENSATION

FIELD OF THE INVENTION

The present invention relates generally to devices and methods for inspecting oral structures. In particular, the present invention relates to devices and methods concerning the examination of tooth surfaces, the tongue, gingivae, cheeks, interior of teeth, dentures, crowns, bridges, and any other oral structures by inducing autofluorescence, viewing it through a filter, then changing the light incident on the mouth structures to compensate for attenuation by the filter.

BACKGROUND

In the field of dental implements, it will be appreciated that various devices may be used to detect abnormal and healthy tooth surfaces. In some instances the difference between abnormal and healthy tooth surfaces may be difficult to distinguish with the naked eye. In addition to simply identifying the abnormal and healthy tooth surfaces, it may further be difficult for a dentist of hygienist to identify where healthy tooth surfaces and abnormal surfaces begin.

U.S. Pat. No. 7,813,787 describes a dental implement method for tooth surface inspection. In particular, it describes a light source body having a handle portion. The light source body includes a switch for selectively energizing and de-energizing a blue light source. The implement includes a yellow filter that is detachable from the implement body. The implement may include glasses containing the yellow filter for filtering fluorescence to be viewed. Using this disclosed implement through the yellow filter glasses, however, colors are changed and non-fluorescent examination of the mouth is impaired.

European application publication EP 2 078 493 A2 describes an apparatus for taking images of a tooth, comprising a plurality of illumination apparatuses and a UV-blocking but blue-light-passing filter situated between the tooth and the sensor.

While a variety of dental implements have been made and used, it is believed that no one prior to the inventor has made or used an invention as described herein.

SUMMARY

An exemplary dental implement is shown having body with a handle and an arm. The dental implement is able to direct blue light into the mouth of a patient. The blue light is absorbed and then re-emitted by porphyrins produced by active bacteria or other abnormal structures within the intra-oral cavity. The user can then view the mouth through a filter and clearly see the porphyrins or other abnormal features as revealed by the re-emitted light.

The user may then wish to view the mouth or other objects in the environment under white-light conditions and may do so without removing the filter used to visualize abnormal features by turning on a second light of the dental implement. The second light in at least some instances is directed through a second filter such that the filtered second light compensates for the first filter. As a result, the user can visualize the mouth and tooth surfaces or other objects as if under white-light conditions, yet without removal of the first filter.

BRIEF DESCRIPTION OF THE DRAWINGS

It is believed the present invention will be better understood from the following description of certain examples taken in conjunction with the accompanying drawings, in which like reference numerals identify the same elements and in which.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from this description. As will be realized, the invention is capable of other different and obvious aspects, all without departing from the invention. Accordingly, the drawings and descriptions should be regarded as illustrative and not restrictive in nature.

It should be understood that, in this description, "visualization" refers to any process or means by which light or an image reaches a person's eye, whether directly or indirectly through optical elements and/or capture and display. A "path" taken by light or an image likewise may include one or more optical elements (lens, mirrors, and filters, as non-limiting examples) and elements that capture, record, and/or playback an image (e.g., CCD's, encoders, decoders, data transmission devices, display devices, and the like). Finally, a "substantially white spectrum" is defined as a spectrum that, when emitted to the eye, is perceived as white light.

In examining tooth surfaces or other oral surfaces or tissues within a patient's mouth, one exemplary way of visualizing tooth surfaces includes using Quantitative Light-induced Fluorescence ("QLF") to provide visualization of various abnormal aspects within the patient's mouth. QLF generally involves directing a light into the mouth of a patient. In many cases, the light used is a strong blue light having a peak wavelength of approximately 405 nm, though it will be appreciated that other suitable peak wavelengths could be used. Porphyrins are produced by the active bacteria in the mouth. After exposing porphyrins to the blue light, these porphyrins will fluoresce. As a result, active bacteria within the mouth may be indirectly visualized by viewing the areas of the mouth exposed to blue light. Visualization is improved with a lens or filter operable to filter out a portion of the light spectrum such that the porphyrins can be easily seen through the filter. As a result, using QLF, a user can visualize lesions, plaque, stains, or any other abnormal tooth conditions or deposits on or inside the teeth or gingiva.

Generally speaking, a handheld dental implement may be used to introduce light or blue light into the mouth of the patient. The handheld dental implement may be operated by a dentist, hygienist, or other user. Furthermore, the handheld dental implement may also be used in a self-examination context where the user, perhaps with the assistance of a mirror or other suitable tool for self visualization, uses the handheld dental implement to visualize abnormal tooth surface conditions. It will be understood that in some variations, light may be applied into the mouth region of the patient using a stationary implement which could be manually, remotely, or otherwise operated by a user. While the dental implement may be used to cause areas within the mouth to fluoresce by exposing them to blue light, it will be understood that in order to survey the mouth more thoroughly, the user may also wish to view the mouth under what are effectively white-light conditions. As a result, it may be desirable for the dental implement to alternatively provide both blue light and compensated white light so that the user can switch between both lighting conditions as desired without removing the filter used for QLF.

I. Exemplary Dental Implement

Figure 1:
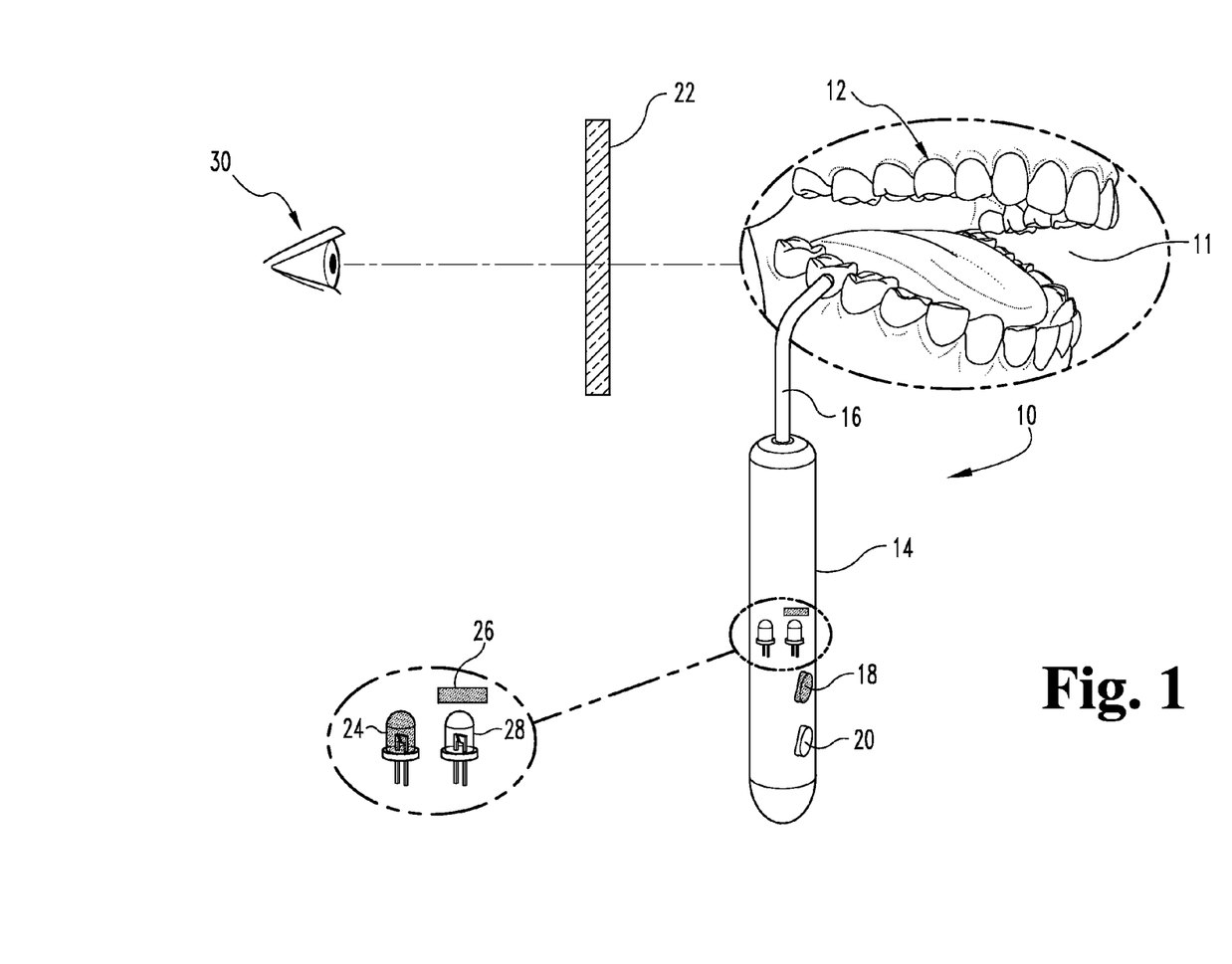
FIG. 1 depicts a diagrammatic view of an exemplary dental implement for use with a patient.

Turning now to FIG. 1, an exemplary dental implement 10 is shown. Generally, dental implement 10 may be used to emit a light, such as the blue light discussed above, to cause porphyrins or other relevant abnormalities to auto-fluoresce. The user aims dental implement 10 such that light is directed at oral tissues, for example, tooth surfaces of a patient's teeth 12 within the patient's mouth 11. Dental implement 10 includes a wand having a handle portion 14 connected to an arm 16. Arm 16 of the illustrated embodiment includes an angled rod able to deliver light to the mouth for visualization of teeth 12 along with abnormal conditions of teeth 12. Arm 16 may define any suitable angle relative to the axis of handle portion 14 for properly positioning arm 16 within mouth 11. It will be understood that arm 16 may include any shape including a straight rod, bendable member, knob, or any other suitable structure as would be apparent to one of ordinary skill in the art in view of the teachings herein. Handle portion 14 is shown as a cylindrical member operable to be held by a user. However, other suitable shapes may be used as well. For instance, handle portion 14 may have a contoured shape such that the user can comfortably hold handle portion 14.

Handle portion 14 of dental implement 10 in this embodiment also includes a first switch 18 that a user may actuate. Upon actuating first switch 18, a light is emitted from dental implement 10. In particular, in the exemplary embodiment, upon actuating first switch 18, a first LED 24 illuminates and transmits light through arm 16. Thereafter, the light is emitted from arm 16 into mouth 11. Furthermore, in the exemplary embodiment shown, a blue light having a wavelength of approximately 405 nm is emitted by first LED 24. While the illustrated embodiment uses an LED for first LED 24, it is understood that first switch 18 may trigger a laser, OLED, bulb, or any other light-producing structure able to transmit light through arm 16 directed into mouth 11. In addition, the embodiment shown depicts first LED 24 being positioned within handle portion 14, but it will be understood that first LED 24 may also be located in arm 16, on glasses wearable by the user, or in any other suitable location as would be apparent to one of ordinary skill in the art in view of the teachings herein.

Arm 16 assists in directing light at the surface of teeth 12. Upon re-actuating first switch 18, first LED 24 turns off and blue light is no longer emitted from arm 16. While the illustrated embodiment shows first switch 18 having a button-like construction, it will be understood that first switch 18 may include a slider switch, rotating switch, capacitive or resistive touch switch, or any other suitable switch type. Upon actuating first switch 18 and directing light onto the surface of teeth 12, abnormal structures or substances on teeth may absorb emitted blue light. Thereafter, a portion or all of those abnormal structures or substances auto-fluoresce with intensity peaks in the green and red ranges of visible light. It will be understood that structures that auto-fluoresce due to blue light emission may be visualized as red using filter 22 positioned between mouth 11 and the eyes 30 of the user.

Figure 2:
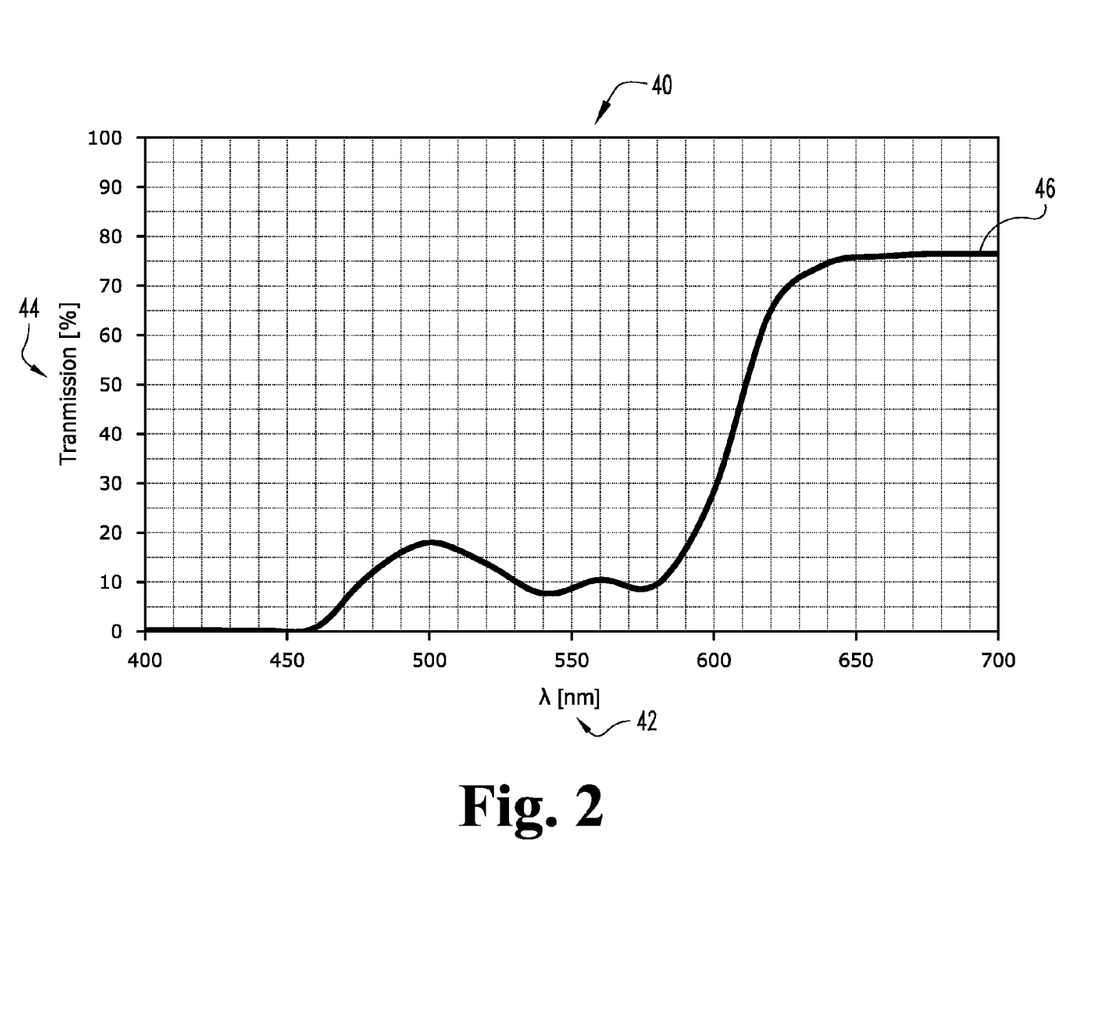
FIG. 2 depicts a graph view of the transmission spectrum of the filter 22 of FIG. 1.

Filter 22 includes a naked lens, but may include glasses outfitted with filter 22. Filter 22 may be outfitted on a dental loupe or dental microscope. It will be understood that other ways of filtering particular frequencies of light may be used. In this embodiment, filter 22 filters frequencies as shown in FIG. 2, which will be discussed in further detail below.

During the use of dental implement 10, it will be understood that the user may wish to view the surface of teeth 12 under normal white-light conditions. Furthermore, the user may wish to alternate between white-light and blue-light views during the inspection of teeth 12 within mouth 11 without removing filter 22 from the user's line of sight. In addition to first switch 18, which may be used to control the emission of blue light from dental implement 10, dental implement 10 also includes a second switch 20 able to control emission of "compensated white light."

In this embodiment, second switch 20 may be actuated to illuminate a second LED 28, which is filtered by filter 26 to emit light that, when viewed through filter 22, is substantially white light. As discussed above with respect to first LED 24, second LED 28 need not necessarily include an LED or only an LED. In other exemplary embodiments, second LED 28 may alternatively or additionally include a laser, OLED, bulb, or any other suitable light-emitting source. Second LED 28 is further in optical communication with compensating filter 26.

In the illustrated embodiment, dental implement 10 is shown having first switch 18 and second switch 20 positioned side by side. Indeed, other suitable configurations may be used as well. For instance, first switch 18 and second switch 20 may be implemented as a three-way switch or rocker to control the illumination of second LED 28 and first LED 24 in a single element. First switch 18 and second switch 20 may be positioned such that they rest side by side laterally rather than longitudinally along the length of handle portion 14. First switch 18 and second switch 20 may be integrated into a touch screen or other suitable switch rather than one that mechanically actuates. Furthermore, second switch 20 may be configured such that actuating second switch 20 simultaneously turns second LED 28 on and turns first LED 24 off.

Compensating filter 26 is shown as a filter located between second LED 28 and mouth 11. Compensating filter 26 is shown in the illustrated embodiment as a lens positioned in front of second LED 28, but it will be understood that compensating filter 26 may include other suitable variations such as a filter paint, a coating that covers second LED 28, or a material integrally formed with second LED 28, yet is operable to filter certain frequencies. In yet other variations, compensating filter 26 may include a "light interference filter" that intersects the light emitted by second LED 28 to filter or cancel particular wavelength ranges. As a result, compensating filter 26 in conjunction with second LED 28 is able to compensate for the effect of filter 22. Thus, when second LED 28 is turned on, the user can look into mouth 11 through filter 22 and visualize the inside of mouth under what is effectively white-light or near white-light conditions without having to remove filter 22. Such visualization can occur in response to the user actuating second switch 20.

In order to understand the mechanics of compensating filter 26 compensating for filter 22, the following discusses the transmission profiles of the various filters of dental implement 10.

FIG. 2 depicts an exemplary graph 40 showing the transmission profile of exemplary filter 22. In particular, the horizontal axis 42 shows the various wavelengths that may reach filter 22. The vertical axis 44 shows the amount of light transmitted through filter 22 at the various wavelengths in terms of percentage transmission. Plot line 46 depicts the percentage of transmission of light at wavelengths between 400 nm and 700 nm. As can be seen from graph 40, filter 22 is characterized by allowing almost no transmission through filter 22 at wavelengths between 400 nm and 450 nm, roughly the violet range of the visible spectrum. Filter 22 is further characterized by having a relatively low transmission rate at wavelengths between 470 nm and 600 nm, which includes the blue, green, yellow and a portion of the orange ranges of the visible spectrum. Finally, as the wavelength increases beyond 600 nm, the orange and red portions of the visible spectrum, the transmission of light through filter 22 rises to approximately 75-80%. As a result, when blue LED 24 is illuminating mouth 11, and a user looks into mouth 11 through filter 22, the porphyrins emit light with a strong band in the low-wavelength region and another strong band in the high-wavelength region, but the user primarily sees that decay as bright red.

Figure 3:
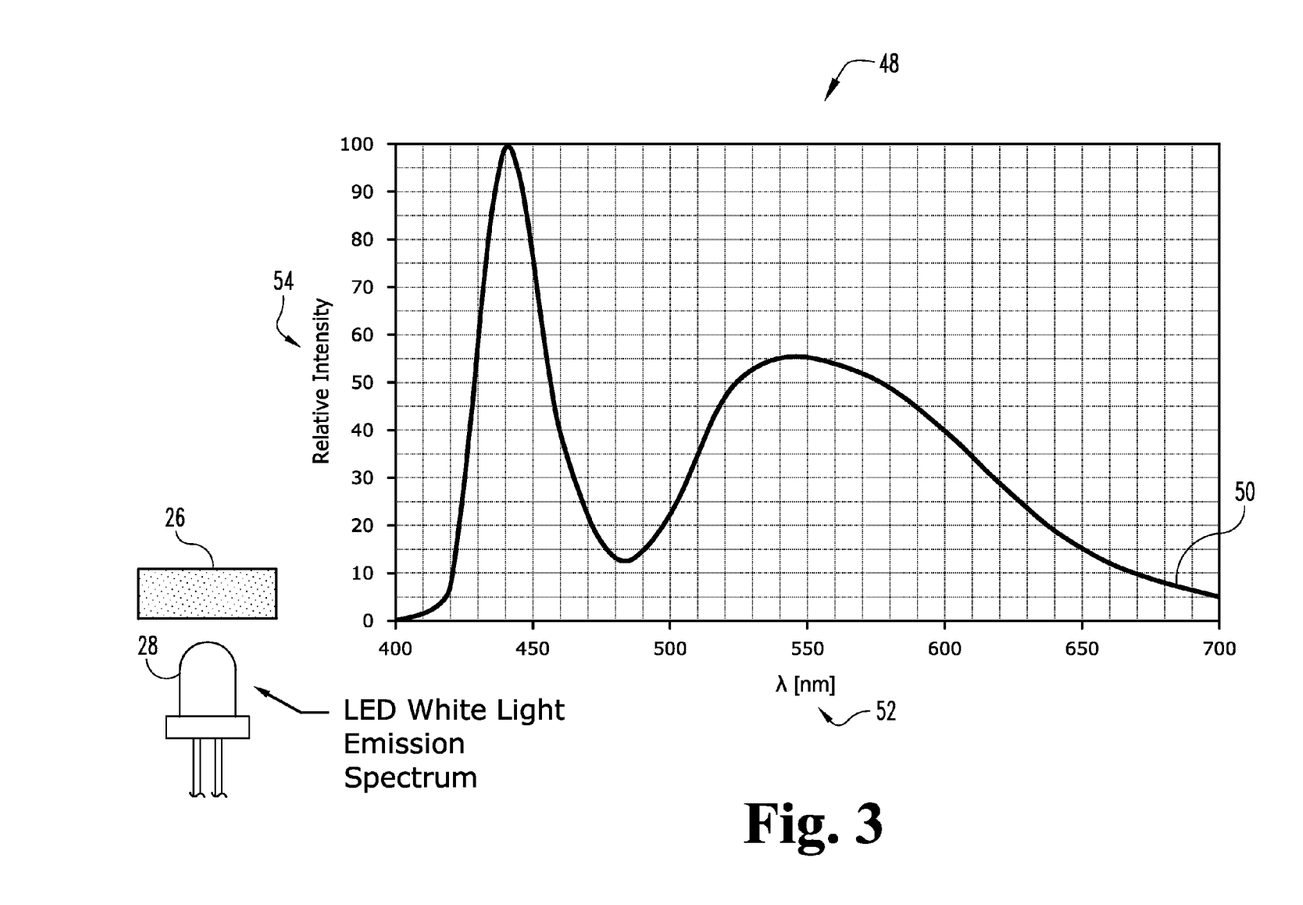
FIG. 3 depicts a graph view of the relative intensity spectrum of the second LED 28 of FIG. 1.

Turning now to FIG. 3, another graph 48 is shown that depicts an emission spectrum of light produced in the illustrated embodiment by second LED 28 (which was shown in FIG. 1). The horizontal axis 52 depicts wavelengths between 400 nm and 700 nm. The vertical axis 54 shows the relative intensity of the light produced by the second LED 28 as a value between 0 and 100. As can be seen from plot line 50, the relative intensity of second LED 28 peaks around 405 nm (in the violet range) and has another region of significant intensity in the wider band between 500 nm and 600 nm (mostly green and yellow).

Figure 4:
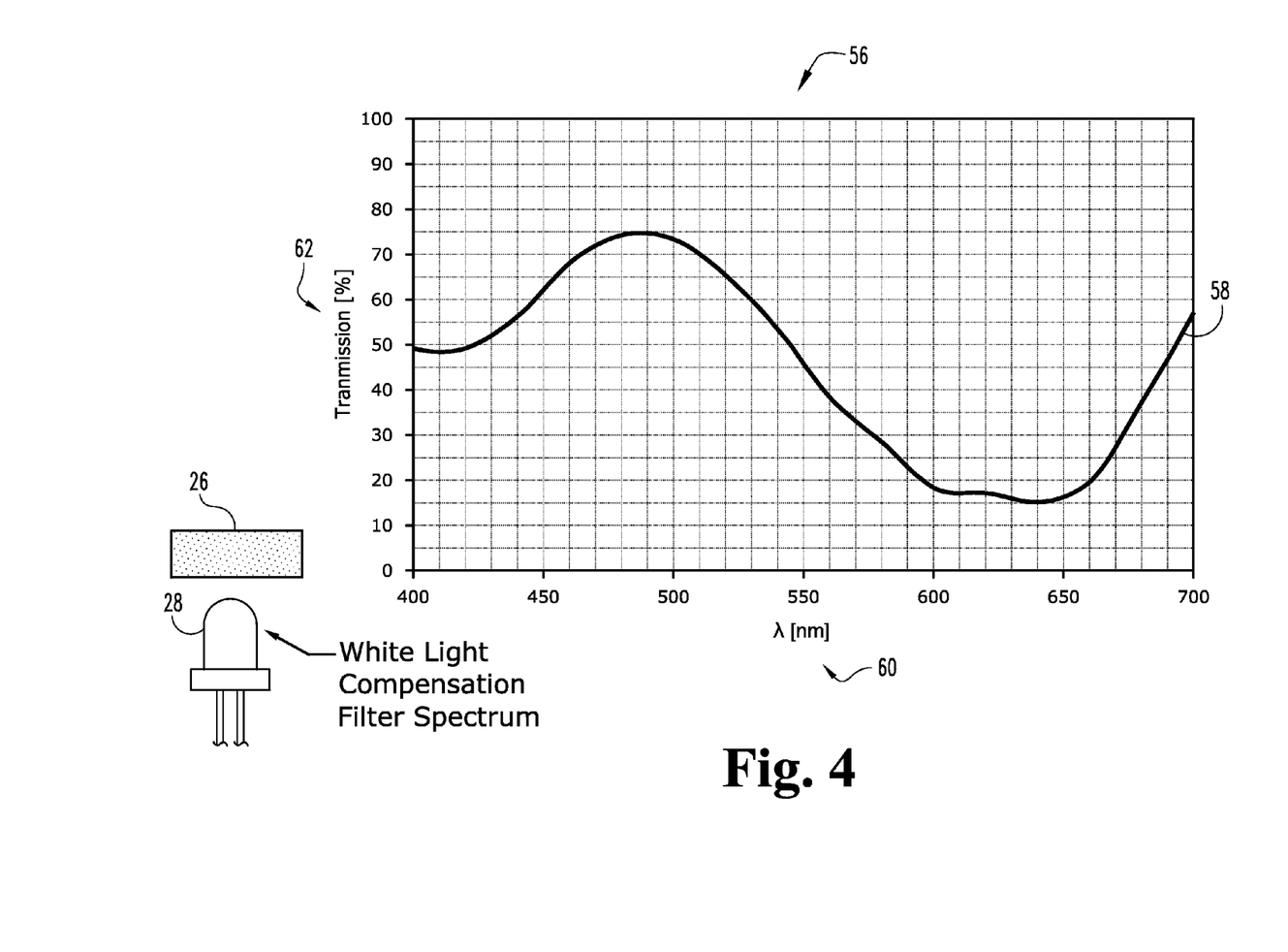
FIG. 4 depicts a graph view of the transmission spectrum of the white light filter 26 of FIG. 1.

FIG. 4 shows a graph 56 of the transmission percentage of compensating filter 26 (shown in FIG. 1) at wavelengths between 400 nm and 700 nm. The horizontal axis 60 shows the various wavelengths between 400 nm and 700 nm. The vertical axis 62 shows transmission percentages between 0 and 100% of compensating filter 26. Plot line 58 shows the various transmission percentages at wavelengths between 400 nm and 700 nm. As can be seen from plot line 58, a wider band of transmission is shown at wavelengths between 400 nm and 550 nm (violet, blue, and green). Plot line 58 then dips around wavelengths between 600 nm and 650 nm (orange and orange-red), and increases transmission at wavelengths over 650 nm (red).

The composite of plot 50 (in FIG. 3, light emitted by second LED 28), plot 58 (in FIG. 4, transmission by compensating filter 26), and plot 46 (in FIG. 2, transmission by filter 22) is approximately a flat spectrum. This composite would illustrate illumination by the combination that approximates white-light illumination of mouth 11.

Figure 5:
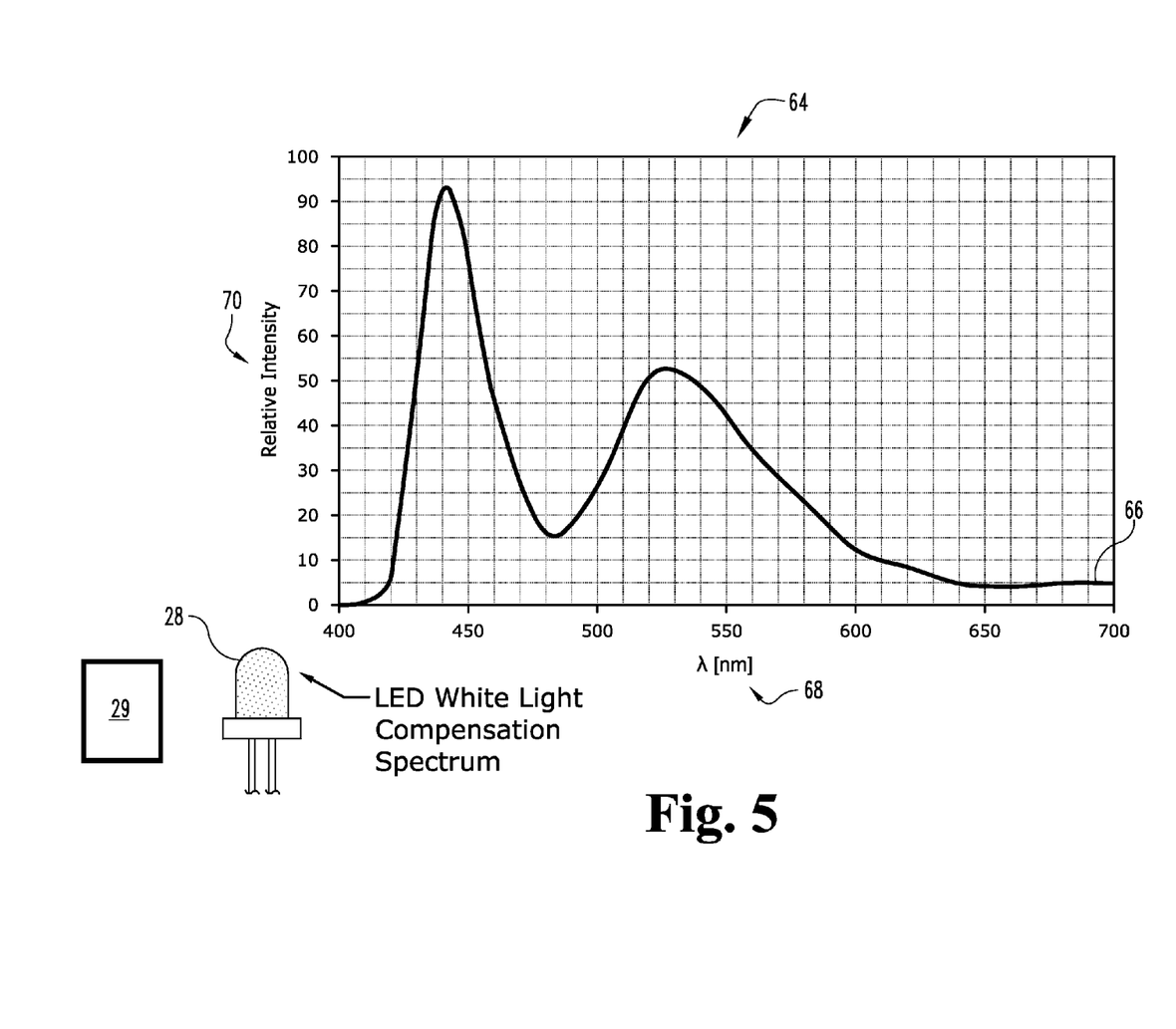
FIG. 5 depicts a graph view of the relative intensity spectrum of an LED, in which the optical characteristics of the second LED 28 and white-light filter 26 are combined, transmitting substantially white light through compensating filter 22 of FIG. 1.

Finally, as an alternative to second LED 28 and compensating filter 26, FIG. 5 shows a graph 64 of a compensating spectrum that represents the light spectrum emitted by a filtered LED 29, which has a built-in filter. Filtered LED 29 produces a comparable spectral emission as the combination of second LED 28 and compensating filter 26 (shown in FIG. 1), as will be understood by those skilled in the art. Similar to graph 48 shown in FIG. 3, graph 64 is shown in terms of relative intensity. For instance, horizontal axis 68 shows various wavelengths between 400 nm and 700 nm. Vertical axis 70 shows the relative intensity of light emitted by filtered LED 24. Plot line 66 shows the relative intensity of filtered LED 24 at each given wavelength.

As can be seen when comparing graph 40 of FIG. 2 and graph 64 of FIG. 5, when the user examines a mouth using a blue light as seen through filter 22, some distortion of the color spectrum results. Still, the user may wish to view mouth 11 as if illuminated by white light. Therefore, the user may turn on second LED 28 to shine second LED 28 through compensating filter 26 and into the mouth 11 while turning the blue light off. Light emitted by second LED 28 shines through compensating filter 26 and, as a result, compensates for portions of the light spectrum attenuated by filter 22. Consequently, the user is able to view the area of the mouth 11 under white-light conditions without removal of filter 22 from his or her line of sight. This may be useful in instances where filter 22 is incorporated into glasses worn by the user that may be cumbersome to remove or other situations where filter 22 may not be easy to remove.

II. Exemplary Integrated Filter and Dental Implement

Figure 6:
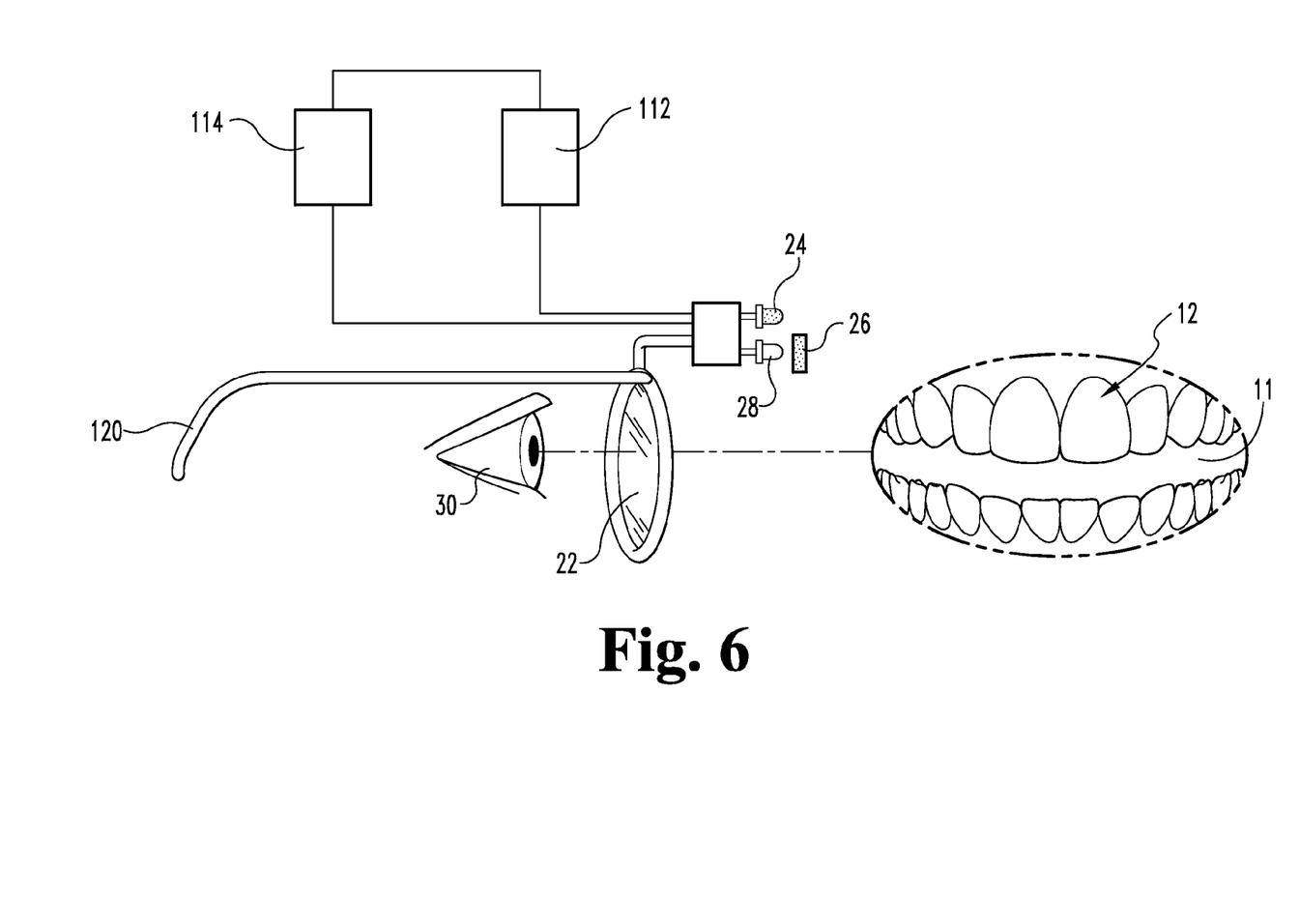
FIG. 6 depicts a diagrammatic view of an alternative exemplary dental implement for hands-free use.

It will be understood that in some instances, it may be desirable to remove the aspect of manually operating dental implement 10. FIG. 6 depicts an alternative version of a dental implement 110 operable to be integrated, attached, or removably attached to glasses 120. While the illustrated embodiment shows dental implement 110 attached to glasses 120, it will be appreciated that dental implement 110 may be attached to any suitable head-mounted object. For instance, instead of glasses 120, dental implement 110 may be attached to a hood, helmet, visor, or any other suitable object as would be apparent to one of ordinary skill in the art in view of the teachings herein.

Dental implement 110 includes first LED 24 and second LED 28 with compensating filter 26 as were discussed previously with respect to FIG. 1. Dental implement 110 further includes a control box 112 and power source 114. Control box 112 may include buttons, switches, rockers, touch screens in combination with haptic feedback, foot pedals, or any other suitable actuation devices such that the user may operate dental implement 110 in a similar manner as dental implement 10 shown in FIG. 1. Furthermore, control box 112 may be separately attached to glasses 120 as shown in the illustrated embodiment or may alternatively be integrated with glasses 120. For instance, control box 112 may be located or integrated with glasses 120 such that the user can readily turn on and off first LED 24 and second LED 28 to turn on the blue light and white light transmitted through compensating filter 26.

Power source 114 may include a battery, an adapter for connecting dental implement 110 into a standard outlet, or any other suitable power source as would be apparent to one of ordinary skill in the art in view of the teachings herein. Furthermore, while the illustrated embodiment shows power source 114 and control box 110 as separate structures, it will be understood that power source 114 and control box 110 may be integrated into a single device and further may be integrated into glasses 120 or otherwise removably attached to glasses 120.

It will further be understood that dental implement 110 may function in a manner substantially similar to that of dental implement 10 of FIG. 1. Due to dental implement 110 being attached or otherwise in communication with glasses 120, the user can look through filter 22 at teeth 12 within mouth 11 of a patient without necessarily having to hold a second implement. Furthermore, the user may then control first LED 24 and second LED 28 to view mouth 11 under blue-light or compensating white-light conditions again without manually operating another device, thereby allowing the user to view mouth 11 through filter 22 under different lighting conditions (blue-light and/or white-light conditions) in a hands-free or substantially hands-free operation, at least with respect to dental implement 110.

In various uses, the systems and methods described herein are applied to tooth surfaces, the tongue, gingivae, cheeks, interior of teeth, dentures, crowns, bridges, and any other oral structures, as will occur to those skilled in the relevant art.

III. Exemplary Procedure With Dental Implement

Dental implement 10 may be used in a variety of ways. For instance, in one exemplary method of use, dental implement 10 may be positioned near mouth 11. Arm 16 may then be positioned near or within mouth 11. The user need not necessarily have an area intended for examination. For example, the user may simply want to survey the entire mouth or alternatively may focus on a specific area for examination. The user grips and moves handle 14 to position arm 16 at an appropriate location to illuminate the desired structure or region.

The user then turns on blue light by actuating first switch 18, which illuminates first LED 24. First LED 24 shines a blue light through arm 16 and into mouth 11. Porphyrins or other abnormal structures fluoresce, and that fluorescence can be seen by the user's eyes 30 looking through filter 22. Thereafter, if the user wishes to view inside of mouth 11 or areas of teeth 12 under white-light conditions, the user actuates second switch 20. Actuating second switch 20 extinguishes first LED 24 and illuminates second LED 28, shining light through compensating filter 26 to produce compensated white light. As a result, the user can view mouth 11 and teeth 12 as if under white light without a filter, yet without having to remove filter 22. If the user wishes to return to visualizing mouth 11 and teeth 12 under a filtered blue-light view, then the user can actuate second switch 20 again to turn off second LED 28. First switch 18 may be actuated again in order to turn off blue light emitted by first LED 24.

In various alternative embodiments, filter 22 is made integral to arm 16 or body 14, while in others it is separate or separable, and in still others it is reattachable. In some alternative embodiments, separate light sources produce the blue light and compensated white light, while in others the two kinds of light are produced by a single light source that is selectably filtered and/or selectably energizes one or more filaments or other light-producing structures.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of any claims that may be presented and is understood not to be limited to the details of structure and operation shown and described in the specification and drawings.

Furthermore, the attached Appendix is merely exemplary and does not necessarily limit the scope of the present invention to any particular embodiment shown in the Appendix. It will be understood that such embodiments in the attached Appendix are merely illustrative.

What is claimed is:

1. An apparatus for assisting a user in visually observing oral structures, comprising:
   a first light source that, when energized, emits visible light characterized by a first spectrum adapted to induce autofluorescence by tissue;
   a first filter in the optical path between the tissue and a user's eye, wherein induced autofluorescence emitted by healthy tissue, when passed through the first filter, is more visually distinguishable from induced autofluorescence emitted by unhealthy tissue; and
   a second light source that, when energized, emits light characterized by a second spectrum, where light characterized by the second spectrum, if it were passed through the first filter, would then have a substantially white spectrum.

2. The apparatus of claim 1, further comprising a photodetector in the path from the first filter to the user's eye.

3. The apparatus of claim 1, wherein there is no photodetector in the path from the first filter to the user's eye.

4. The apparatus of claim 1, wherein the second light source comprises the first light source and a second filter.

5. The apparatus of claim 1, wherein the second light source comprises the first light source and a supplemental light source.

6. The apparatus of claim 1, wherein energizing the second light source de-energizes the first light source.

7. A method for observing oral structures, comprising the steps of:
   energizing a first light source that emits visible light characterized by a first spectrum adapted to induce autofluorescence by tissue;
   visualizing the tissue through a first filter in the optical path between the tissue and a user's eye, wherein, when passed through the first filter, the induced autofluorescence by healthy tissue is more visually distinguishable from induced autofluorescence by unhealthy tissue; and
   energizing a second light source that emits light characterized by a second spectrum, wherein light characterized by the second spectrum, if it were passed through the first filter, would then have a substantially white spectrum.

8. The method of claim 7, further comprising using a photodetector to detect an image comprising the autofluorescence after the autofluorescence passes through the first filter.

9. The method of claim 8, further comprising displaying the image.

10. The method of claim 8, further comprising storing the image.

11. The method of claim 7, further comprising:
    capturing first video in substantially real time while the first light source is energized, where the first video comprises a plurality of images of the autofluorescence after the autofluorescence passes through the first filter; and capturing second video in substantially real time while the second light source is energized, where the second video comprises a plurality of images of the tissue taken through the first filter.

12. The method of claim 7, wherein there is no photodetector in the path from the first filter to the user's eye.

13. The method of claim 7, wherein the second light source comprises the first light source and a second filter.

14. The method of claim 7, wherein the second light source comprises the first light source and a supplemental light source.

15. The method of claim 7, wherein energizing the second light source substantially simultaneously de-energizes the first light source.

* * * * *